US00PP21447P2

(12) United States Plant Patent
Smith

(10) Patent No.: US PP21,447 P2
(45) Date of Patent: Nov. 2, 2010

(54) ***BRACHYCOME* PLANT NAMED 'MM001'**
(50) Latin Name: *Brachycome angustifolia*
Varietal Denomination: MM001

(75) Inventor: Kimberley K. Smith, Mt. Eliza (AU)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 0 days.

(21) Appl. No.: 12/459,837

(22) Filed: Jul. 8, 2009

(51) Int. Cl.
*A01H 5/00* (2006.01)

(52) U.S. Cl. ..... Plt./411
(58) Field of Classification Search ..... Plt./411
See application file for complete search history.

*Primary Examiner*—June Hwu
(74) *Attorney, Agent, or Firm*—C. A. Whealy

(57) ABSTRACT

A new and distinct cultivar of *Brachycome* plant named 'MM001', characterized by its compact and mounding plant habit; freely branching growth habit; freely flowering habit; large inflorescences positioned just above the foliage; violet-colored ray florets; and good postproduction longevity.

2 Drawing Sheets

Botanical designation: *Brachycome angustifolia.*
Cultivar denomination: 'MM001'.

BACKGROUND OF THE INVENTION

The present invention relates to a new and distinct cultivar of *Brachycome* plant, botanically known as *Brachycome angustifolia* and hereinafter referred to by the name 'MM001'.

The new *Brachycome* plant is a product of a controlled breeding program conducted by the Inventor in Cranbourne, Victoria, Australia.

The objective of the breeding program is to create new compact *Brachycome* plants with large inflorescences and peduncles.

The new *Brachycome* plant originated from a cross-pollination in Cranbourne, Victoria, Australia, of an unnamed proprietary selection of *Brachycome angustifolia*, not patented, as the female, or seed, parent with *Brachycome angustifolia* 'Billabong Mauve Delight', disclosed in U.S. Plant Pat. No. 10,889, as the male, or pollen, parent. The new *Brachycome* was discovered and selected by the Inventor as a single flowering plant from within the progeny of the stated cross-pollination in a controlled environment in Cranbourne, Victoria, Australia.

Asexual reproduction of the new *Brachycome* plant by vegetative cuttings in a controlled environment in Cranbourne, Victoria, Australia has shown that the unique features of this new *Brachycome* plant are stable and reproduced true to type in successive generations.

SUMMARY OF THE INVENTION

Plants of the new *Brachycome* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'MM001'. These characteristics in combination distinguish 'MM001' as a new and distinct cultivar of *Brachycome:*

1. Compact and mounding plant habit.
2. Freely branching growth habit.
3. Freely flowering habit.

4. Large inflorescences positioned just above the foliage.
5. Violet-colored ray florets.
6. Good postproduction longevity.

Plants of the new *Brachycome* differ from plants of the female parent selection in the following characteristics:

1. Plants of the new *Brachycome* have smaller leaves than of the female parent selection.
2. Plants of the new *Brachycome* have smaller inflorescences than plants of the female parent selection.

Plants of the new *Brachycome* differ from plants of the male parent, 'Billabong Mauve Delight', in the following characteristics:

1. Plants of the new *Brachycome* are taller and more mounding than plants of 'Billabong Mauve Delight'.
2. Plants of the new *Brachycome* are more densely foliated and have larger leaves than plants of 'Billabong Mauve Delight'.
3. Plants of the new *Brachycome* flower earlier than plants of 'Billabong Mauve Delight'.
4. Plants of the new *Brachycome* have larger inflorescences than plants of 'Billabong Mauve Delight'.

Plants of the new *Brachycome* can also be compared to plants of the *Brachycome multifida* 'Metallic Blue', disclosed in U.S. Plant Pat. No. 13,692. In side-by-side comparisons conducted in Cranbourne, Victoria, Australia, plants of the new *Brachycome* differed from plants of 'Metallic Blue' in the following characteristics:

1. Plants of the new *Brachycome* were more compact and more mounding than plants of 'Metallic Blue'.
2. Plants of the new *Brachycome* had broader leaves than plants of 'Metallic Blue'.
3. Plants of the new *Brachycome* were more freely flowering than plants of 'Metallic Blue'.
4. Plants of the new *Brachycome* had shorter peduncles than plants of 'Metallic Blue'.

BRIEF DESCRIPTION OF THE PHOTOGRAPHS

The accompanying colored photographs illustrate the overall appearance of the new *Brachycome* plant, showing the colors as true as it is reasonably possible to obtain in colored reproductions of this type. Colors in the photographs may differ slightly from the color values cited in the detailed botanical description which accurately describe the colors of the new *Brachycome*.

The photograph on the first sheet comprises a top perspective view of a typical flowering plant of 'MM001' grown in a container.

The photograph on the second sheet is a close-up view of typical inflorescences and leaves of 'MM001'.

DETAILED BOTANICAL DESCRIPTION

The aforementioned photographs and following observations, measurements and values describe plants grown in 15-cm containers in Cranboume, Victoria, Australia, under commercial practice during the summer and autumn in a polyethylene-covered greenhouse with day temperatures ranging from 12° C. to 40° C., night temperatures ranging from 6° C. to 28° C. and light levels ranging from 1,000 lux to 9,000 lux. Plants were pinched one time and were six months old when the photographs and description were taken. In the following description, color references are made to The Royal Horticultural Society Colour Chart, 1995 Edition, except where general terms of ordinary dictionary significance are used.

Botanical classification: *Brachycome angustifolia* 'MM001'.

Parentage:

*Female, or seed, parent.*—Unnamed proprietary selection of *Brachycome angustifolia*, not patented.

*Male, or pollen, parent.*—*Brachycome angustifolia* 'Billabong Mauve Delight', disclosed in U.S. Plant Pat. No. 10,889.

Propagation:

*Type.*—By vegetative cuttings.

*Time to initiate roots, summer.*—About 12 to 25 days at temperatures of 22° C. to 30° C.

*Time to initiate roots, winter.*—About 18 to 35 days at temperatures of 15° C. to 22° C.

*Time to produce a rooted young plant, summer.*—About four to six weeks at temperatures of 20° C. to 35° C.

*Root description.*—Thin, wiry to slightly fleshy; white in color.

*Rooting habit.*—Freely branching; moderately dense.

Plant description:

*Plant form and growth habit.*—Compact and mounded plant habit; moderately vigorous growth habit; freely branching habit with numerous lateral branches developing after pinching.

*Plant height.*—About 25 cm to 35 cm.

*Plant width (spread).*—About 40 cm to 60 cm.

*Lateral branches.*—Length: About 3 cm to 8 cm. Diameter: About 1.5 mm. Internode length: About 1 cm to 2 cm. Strength: Moderately strong. Texture: Smooth, glabrous. Color: Close to 137B.

Foliage description:

*Arrangement.*—Alternate, simple; sessile.

*Length.*—About 1.2 cm to 4.7 cm.

*Width.*—About 8 mm to 22 mm.

*Shape.*—Narrowly to broadly wedge-shaped with four to seven oblong lobes.

*Apex.*—Acute to somewhat obtuse.

*Base.*—Attenuate.

*Margin.*—Four to seven-lobed.

*Texture, upper and lower surfaces.*—Smooth, glabrous.

*Venation pattern.*—Pinnate.

*Color.*—Developing leaves, upper surface: Close to 137B. Developing leaves, lower surface: Close to 137D. Fully expanded leaves, upper surface: Close to 137A; venation, close to 137A. Fully expanded leaves, lower surface: Close to 137C to 137D; venation, close to 137C to 137D.

Inflorescence description:

*Appearance and habit.*—Single composite inflorescence form with ray and disc florets; inflorescences borne just above the foliage; freely flowering habit with numerous inflorescences developing per plant during the flowering period.

*Fragrance.*—Not detected.

*Flowering season.*—Plants flower from spring through autumn in Australia; flowering continuous during this period; plants begin flowering about four to eight weeks after planting.

*Inflorescence longevity.*—Inflorescences last about two to four weeks on the plant; inflorescences not persistent.

*Inflorescence bud.*—Height: About 2 mm to 3 mm. Diameter: About 3 mm to 4 mm. Shape: Oblate. Color: Between 138D and 143B.

*Inflorescence size.*—Height: About 7 mm to 8 mm. Diameter: About 2.8 cm to 3.4 cm. Diameter of disc: About 6 mm to 8 mm.

*Ray florets.*—Quantity/arrangement: About 18 to 24 in about two whorls. Shape: Lanceolate, narrowly oblong. Apex: Bluntly acute. Base: Attenuate. Margin: Entire. Length: About 7 mm to 11 mm. Width: About 1.5 mm to 2 mm. Texture, upper and lower surfaces: Smooth, glabrous. Color: When opening, upper surface: Close to 87A to 87B. When opening, lower surface: Close to 71A. Fully opened, upper surface: Close to 87D; color becoming closer to 81D with development. Fully opened, lower surface: Close to 81D.

*Disc florets.*—Arrangement: Massed at center of receptacle. Shape: Tubular, elongated. Apex: Five-pointed. Length: About 4 mm. Width: About 1 mm. Texture: Smooth, glabrous. Color, immature: Close to 144C. Color, mature: Close to 9A.

*Involucral bracts.*—Quantity/arrangement: About 14 to 19 arranged in a single whorl; bracts imbricate. Length: About 2 mm to 3 mm. Width: About 1 mm. Shape: Oblong. Apex: Acute to obtuse. Margin: Entire, fringed. Texture, upper and lower surfaces: Smooth, glabrous; satiny. Color, upper and lower surfaces: Close to 138B.

*Peduncles.*—Length, terminal peduncle: About 3.8 cm to 7.2 cm. Diameter: About 2 mm. Strength: Moderately strong. Texture: Smooth, glabrous. Color: Close to 138A.

*Reproductive organs.*—Present on disc florets only. Androecium: Filament length: Less than 1 mm. Filament color: Close to 155D. Anther length: Less than 1 mm. Anther shape: Oblong to lanceolate. Pollen amount: None observed. Gynoecium: Stigma shape: Bi-lobed. Style length: About 3 mm. Style color: Close to 155D.

*Seeds.*—Seed set is nil to scarce on plants of the new *Brachycome*. Quantity per inflorescence: None to about three. Length: Less than 1 mm. Diameter: Less than 1 mm.

Disease/pest resistance: Plants of the new *Brachycome* have not been observed to be resistant to pathogens and pests common to *Brachycomes*.

Garden performance: Plants of the new *Brachycome* have been observed to have good garden performance and tolerate ram, wind and temperatures ranging from about −3° C. to about 44° C.

It is claimed:

1. A new and distinct *Brachycome* plant named 'MM001' as illustrated and described.

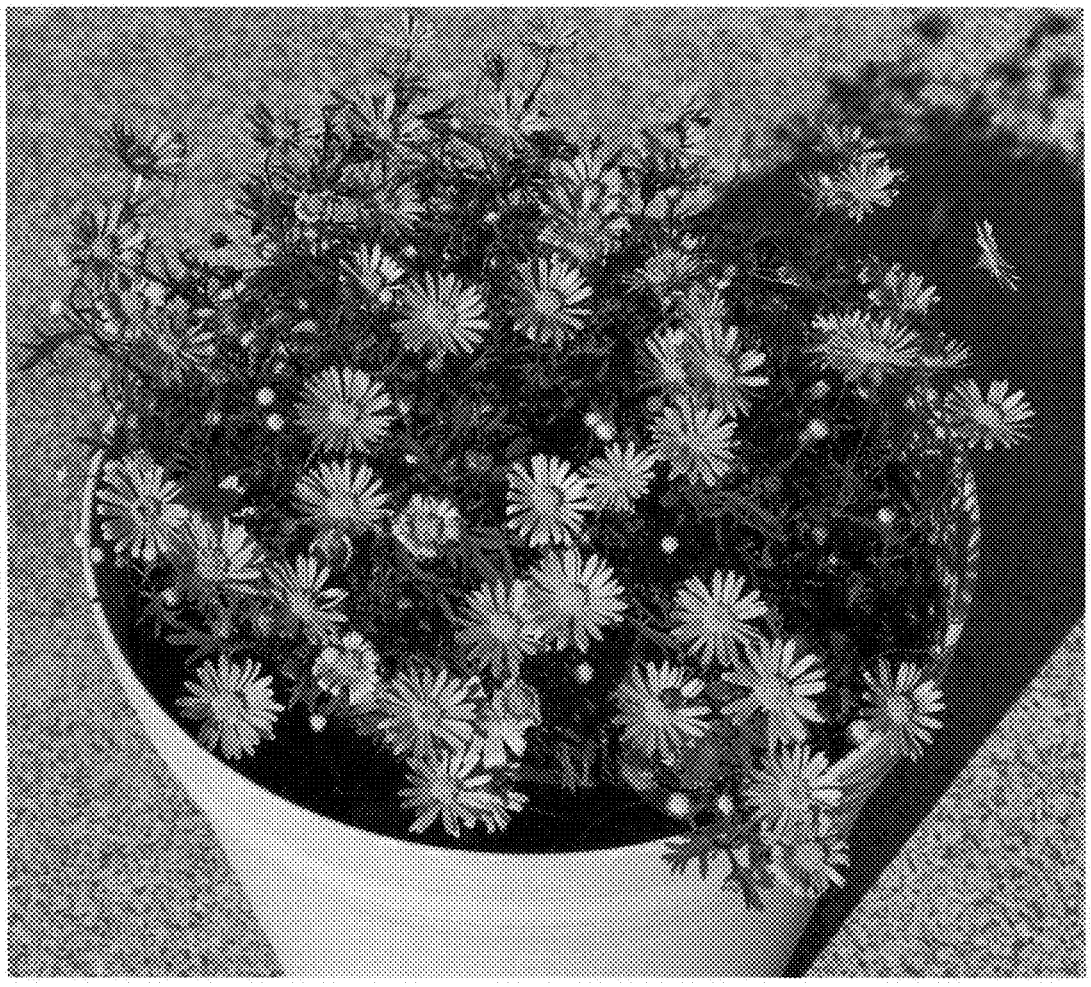

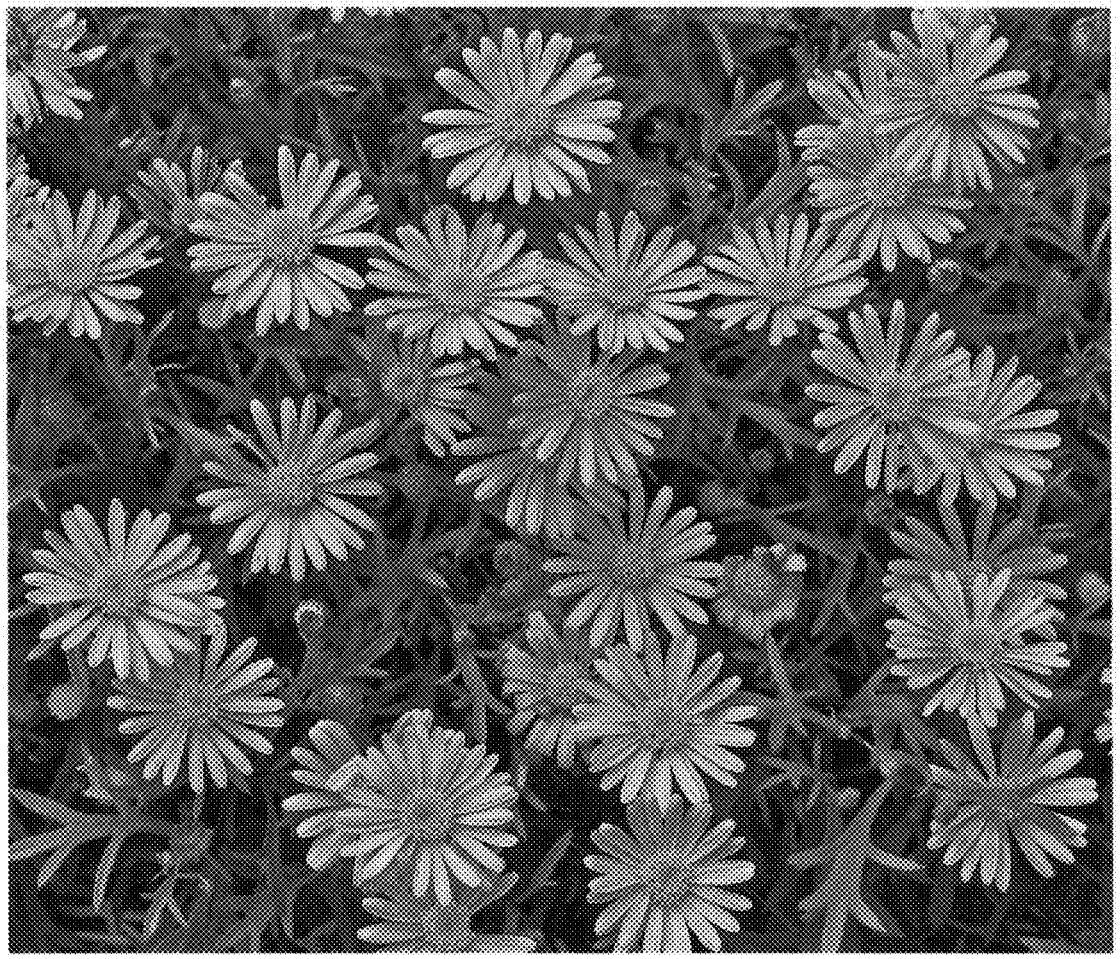

* * * * *